United States Patent
Krüger et al.

[11] Patent Number: 6,130,748
[45] Date of Patent: Oct. 10, 2000

[54] CHEMICAL SENSOR BASED ON POROUS SILICON

[75] Inventors: Michael Krüger, Aachen; Michael Berger, Darmstadt; Markus Thönissen, Nettetal; Rüdiger Arens-Fischer; Hans Lüth, both of Aachen, all of Germany

[73] Assignee: Forschungszentrum Jülich GmbH, Jülich, Germany

[21] Appl. No.: 09/142,423

[22] PCT Filed: Feb. 28, 1997

[86] PCT No.: PCT/DE97/00361

§ 371 Date: Sep. 4, 1998

§ 102(e) Date: Sep. 4, 1998

[87] PCT Pub. No.: WO97/33147

PCT Pub. Date: Sep. 12, 1997

[30] Foreign Application Priority Data

Mar. 5, 1996 [DE] Germany ............ 196 08 428

[51] Int. Cl.⁷ ........................................ G01B 9/02
[52] U.S. Cl. .................................. 356/345; 356/361
[58] Field of Search ............................. 356/345, 352, 356/361; 250/227.19, 227.27; 385/12; 422/82.02, 82.11

[56] References Cited

U.S. PATENT DOCUMENTS

| | | |
|---|---|---|
| 5,082,629 | 1/1992 | Burgess, Jr. et al. . |
| 5,120,131 | 6/1992 | Lukosz .................................. 356/361 |
| 5,377,008 | 12/1994 | Ridgway et al. ..................... 356/361 |
| 5,453,624 | 9/1995 | Sailor et al. . |
| 5,874,047 | 2/1999 | Schoning et al. ................. 422/82.02 |

FOREIGN PATENT DOCUMENTS

| | | |
|---|---|---|
| 38 32 185 A1 | 3/1990 | Germany . |
| 40 33 357 A1 | 4/1992 | Germany . |
| 42 00 088 A1 | 7/1993 | Germany . |
| 44 27 921 A1 | 2/1996 | Germany . |

OTHER PUBLICATIONS

Gauglitz, et al. "Optische Chemo– und Biosensoren für die Umwelt– und Bioanalytik" Spektrum der Wissenschaft, Jan. 1994, pp. 92–97.

Bjorklund, et al. "Color Changes In Thin Porous Silicon Films Caused By Vapor Exposure" Applied Physics Letters, Nov. 1996, pp. 3001–3003.

Homola, et al. "A New Optical Fiber Sensor For Humidity Measurement" pp. 245–248.

Arens–Fischer "Strukturbeeinflussung von Porosem Silicium für Optoelektronische Anwendungen" pp. 83–91.

Primary Examiner—Samuel A. Turner
Attorney, Agent, or Firm—Collard & Roe, P.C.

[57] ABSTRACT

In an analytic process using porous silicon, a substance is detected or its concentration in a fluid is determined based on the change in the optical property of porous silicon as a function of the refractive index of the substance present in the pores of the porous silicon, or of the fluid containing the substance. An analytic device for detecting a substance or for determining the concentration of a substance in a fluid with the use of porous silicon comprises a component at least partly consisting of porous silicon, the optical property of which is dependent upon the refractive index of the substance or of the fluid containing the substance, whereby a change in the optical property of the porous silicon is measurable to indicate detection of the substance or to determine the concentration of such substance in the pores of the porous silicon.

20 Claims, 6 Drawing Sheets

CHEMICAL SENSOR BASED ON POROUS SILICON

BACKGROUND OF THE INVENTION

1. Field of the Invention

The present invention is related to an analytic process using porous silicon for producing a variable refractive index, as well as to an analytic device for such a process according to the introductory part of claim 8.

2. The Prior Art

Porous silicon (PS) is a promising material for applications in sensorics (gas sensors, humidity sensors, biosensors) because of its compatibility with highly developed Si-microelectronics as well as simple manufacturability at favorable cost, whereby use is made of the large inner surface of the material (up to a few 100 $m^2/cm^3$) and the microstructure. Furthermore, layered systems made from PS are excellently suitable for producing optical filters and mirrors as well as wave conductors at favorable cost, whereby air is present in the pores of the PS and the refractive index of the PS is fixed in the course of production by substrate doping, the density of the etching current and the composition of the etching solution.

Porous silicon (PS) consists of a sponge-like structure of silicon crystallites, which is traversed by pores. The size of the crystallites and of the pores varies depending on the doping of the silicon and the manufacturing conditions between a few nanometers and a few micrometers. If the wavelength of light is very much greater than the size of the structures in the PS, the PS appears to the light as a homogeneous material ("effective medium") and its properties therefore can be described by specifying an effective refractive index, which is dependent upon the refractive indices of the silicon crystallites and of the material in the pores.

The structuring of PS by CMOS-compatible process steps has already been demonstrated. Interference filters made from PS, especially Bragg-reflectors and Fabry-Perot filters have already been manufactured as well and are known from M. G. Berger, M. Thonissen, R. Arens-Fischer, H. Munder, H. Luth, M. Arntzen and W. Theiss, Thin Solid Films 255 (1995), pp 313–316. It has been possible already to integrate Bragg-reflectors in a silicon photodiode as a color-selective layer. Furthermore, the conduction of light waves in wave conductors made from PS has been demonstrated.

Now, another possibility to vary the refractive index of the PS consists in filling the pores of the PS with another material instead of air in order to detect substances or to determine their concentration in solutions. This property of the PS has not been put to use heretofore in the state of the art. By using diaphragms with selective permeability on the surface of the PS it is possible to achieve selectivity versus selected substances.

Therefore, the problem of the present invention is to create an analytic process and an analytic device by which a substance can be detected or its concentration can be determined with the use of porous silicon.

SUMMARY OF THE INVENTION

An object according to claim 1 in that a substance is detected or its concentration in a fluid is determined based on the change in the optical property of porous silicon as a function of the refractive index of the substance present in the pores of the porous silicon, or of the fluid containing the substance.

Furthermore, this object is achieved according to the invention in that provision is made for a component which is at least partly made of porous silicon, the optical property of which is dependent upon the refractive index of the substance or of the fluid containi-g the substance, whereby a change in the optical property of the porous silicon can be measured to indicate detection of the substance or to determine the concentration of such substance in the pores of the porous silicon.

For the analytic process as defined by the invention, or for the analytic device as defined by the invention it is proposed that the dependence of the refractive index of the PS upon the refractive index of the material in the pores be put to use for detecting substances or for determining their concentration in solutions. For this purpose the substance not only has to be irreversibly separated (claim 4) in the pores in an advantageous manner but it also can be exchanged (claim 2) in the course of the measuring process in a time-resolved measurement.

Further advantageous developments of the invention in the form of interference filters (claims 9 to 16), wave conductors (claims 17 to 19), interferometers (claims 20 to 25), as well as with a diaphragm with selective permeability (claim 26) are specified in the dependent claims specified above in parentheses.

BRIEF DESCRIPTION OF THE DRAWINGS

Embodiments of the present invention are described in greater detail in the following with the help of drawings, in which.

DETAILED DESCRIPTION OF PREFERRED EMBODIMENTS

Embodiment 1: Color-selective Mirror

Figure 1:
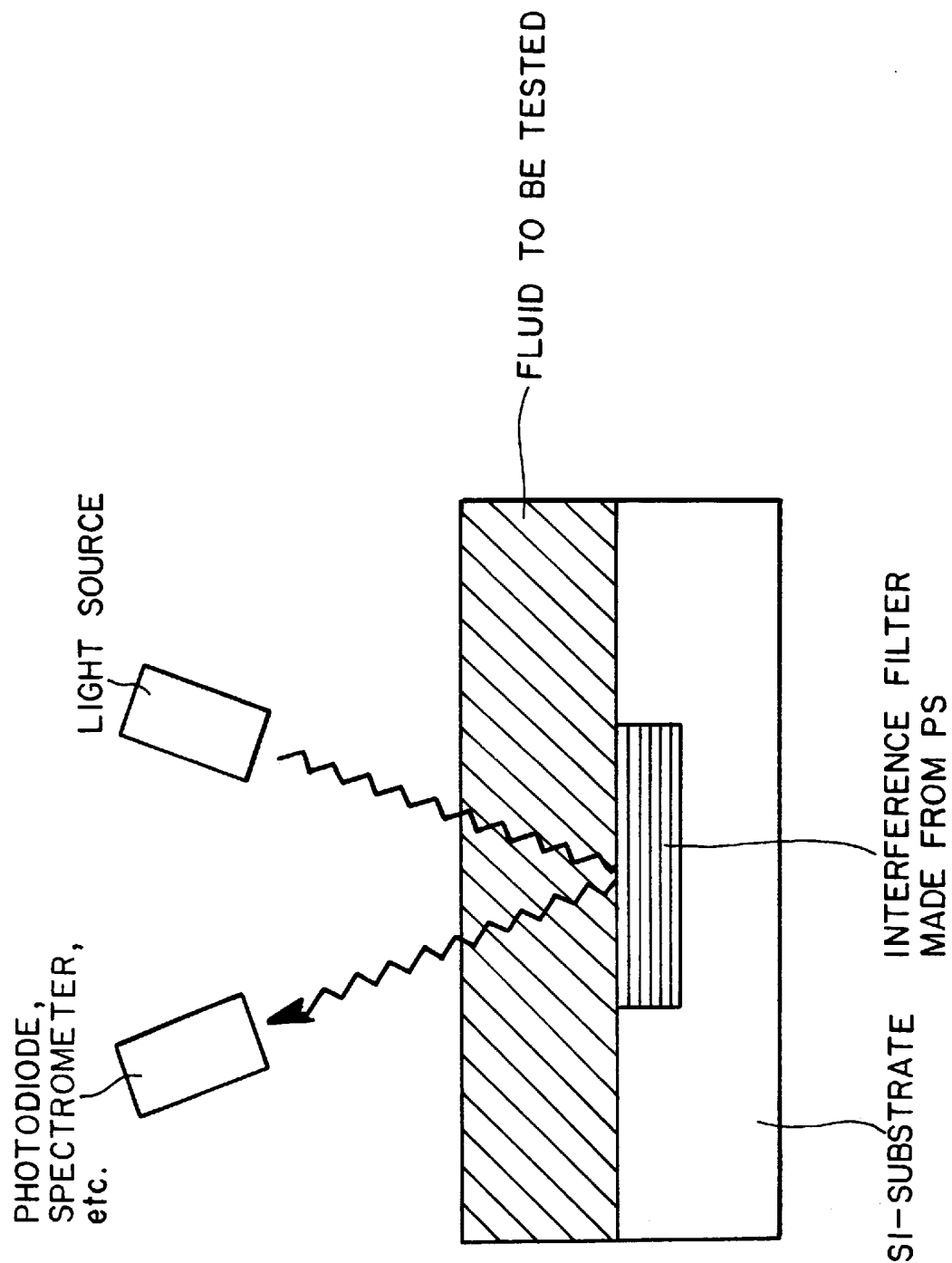
FIG. 1 is a schematic representation of a color-selective reflector made from porous silicon, which reflects the spectral dependence of the refractive power upon the refractive index of the material in the pores.

In the measuring arrangement schematically shown in FIG. 1, an interference filter made from PS is illuminated and the reflected component of the light is measured with a detector. The interference filter serves in this connection as a reflecting filter, the spectral properties of which can be varied by using different PS-layers. If the filter is in a fluid and the latter penetrates the pores of the PS, the spectral reflective power of the filter changes.

Figure 2:
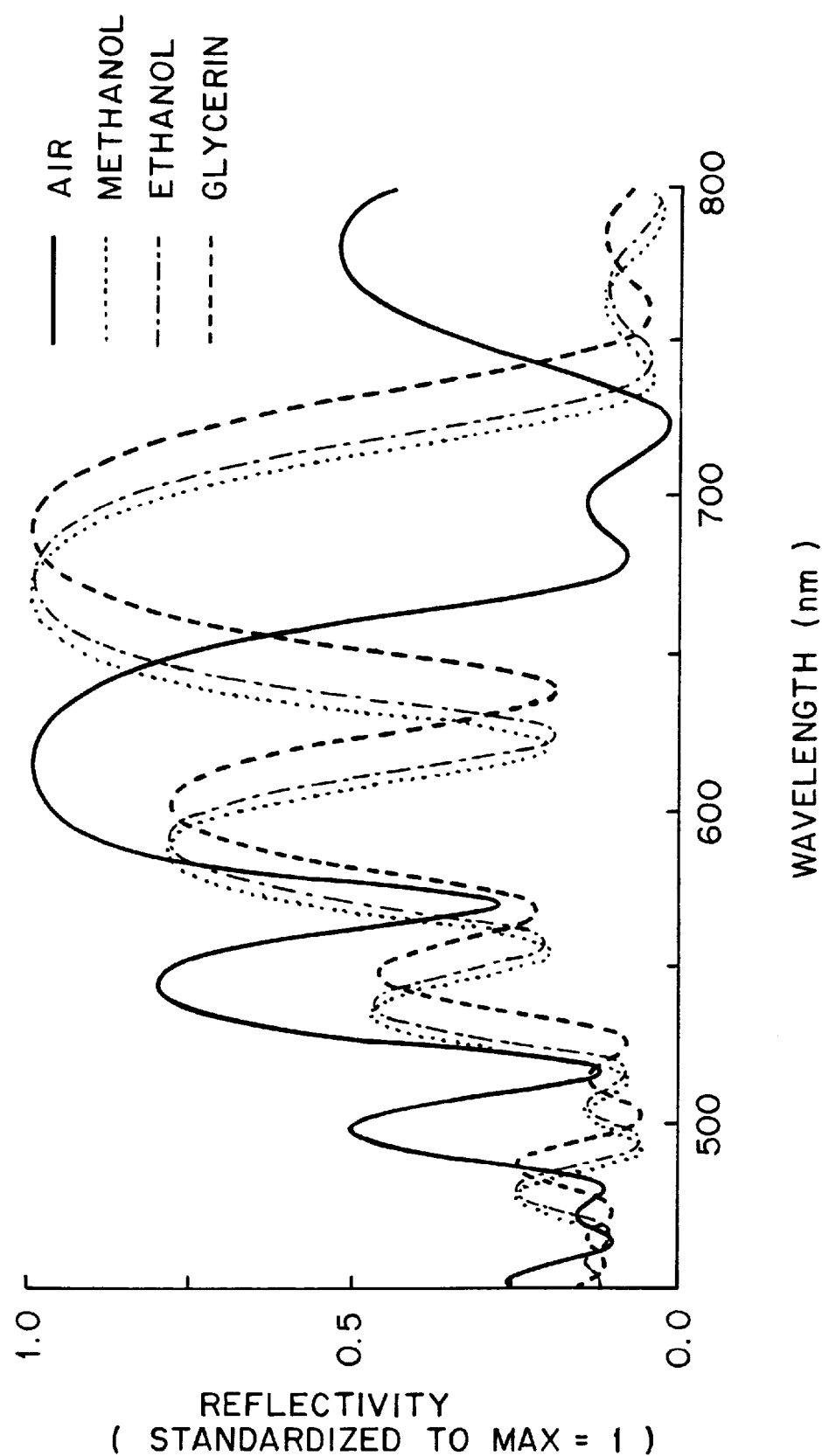
FIG. 2 is a diagram showing measured reflection spectra of a Fabry-Perot filter with different materials in the pores of the porous silicon.

A measurement with such a measuring arrangement is shown in FIG. 2, where the lamp and the detector are integrated in a white-light interferometer. The reflecting filter employed consists of a layered system of the type $[HL]^5[LH]^5$, i.e., a Fabry-Perot filter with 10 periods of the HL-pack. "H" denotes in this connection a layer with a high refractive index, and "L" a layer with a low refractive index. Use is made of a highly p-doped Si-substrate ($1*10$ cm$^{-3}$) and of an etching solution with $H_2O:HF:C_2H_5OH$ at a ratio of 1:1:2. For producing the H-layer, an etching current density of 100 mA/cm$^2$ is used for 0.675s, and for the H-layer analogously 280 mA/cm$^2$ for 0.478s. The filter frequency of the Fabry-Perot filter is shifted as expected toward greater wavelengths as the refractive index of the material in the pores increases (air 570 nm, methanol 621 nm, ethanol 625 nm, glycerin 639 nm).

The reflection spectrum of the interference filter is measured in this measurement over a wide spectral range, which requires the use of a spectrometer. A favorably priced alternative is the use of a laser diode as the light source and of a photodiode as the receiver. In this case, the filter frequency of the interference filter has to be coordinated with the wavelength of the laser. As the laser diode emits monochromatic light, the change in the reflectivity of the filter is measured only for this wavelength, which suffices for characterizing the material in the pores.

Embodiment 2: Color-selective Photodiode

Figure 3:
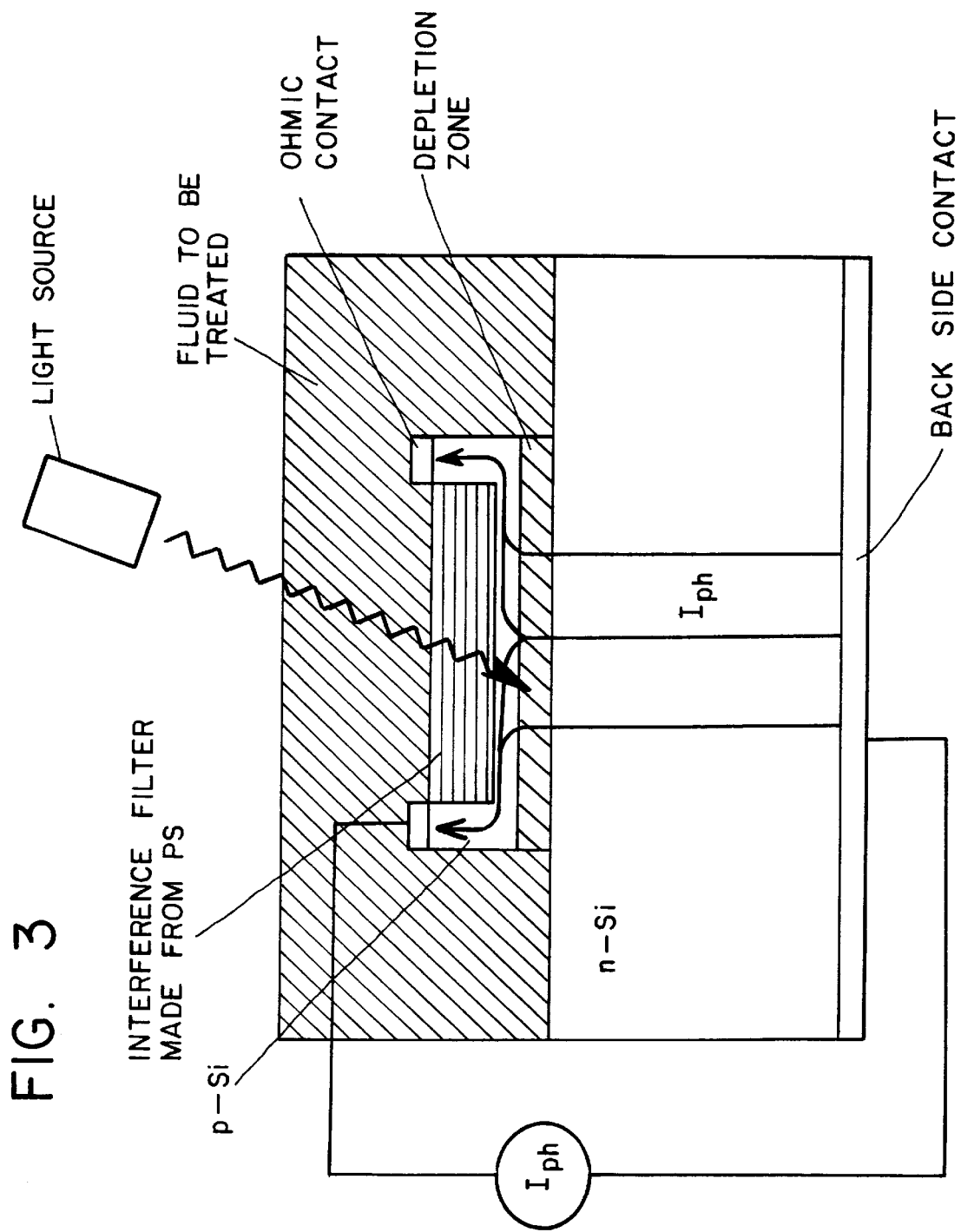
FIG. 3 is a schematic representation of a photodiode with an interference filter made from porous silicon as a color-selective layer, whereby a fluid to be tested penetrates the pores of the porous silicon and changes the refractive index of the porous silicon and thus the optical properties of the interference filter.

Interference filters made from PS can be used also as transmission filters as in FIG. 3 instead of as reflecting filters as in FIG. 1. In the present embodiment, the interference filter is already integrated in an $S_i$-photodiode. When irradiated with monochromatic light, photoelectric current $I_{Ph}$ is a measure for the transmission power of the filter at this wavelength.

Embodiment 3: Maladapted Wave Conductor made from PS

Figure 4:
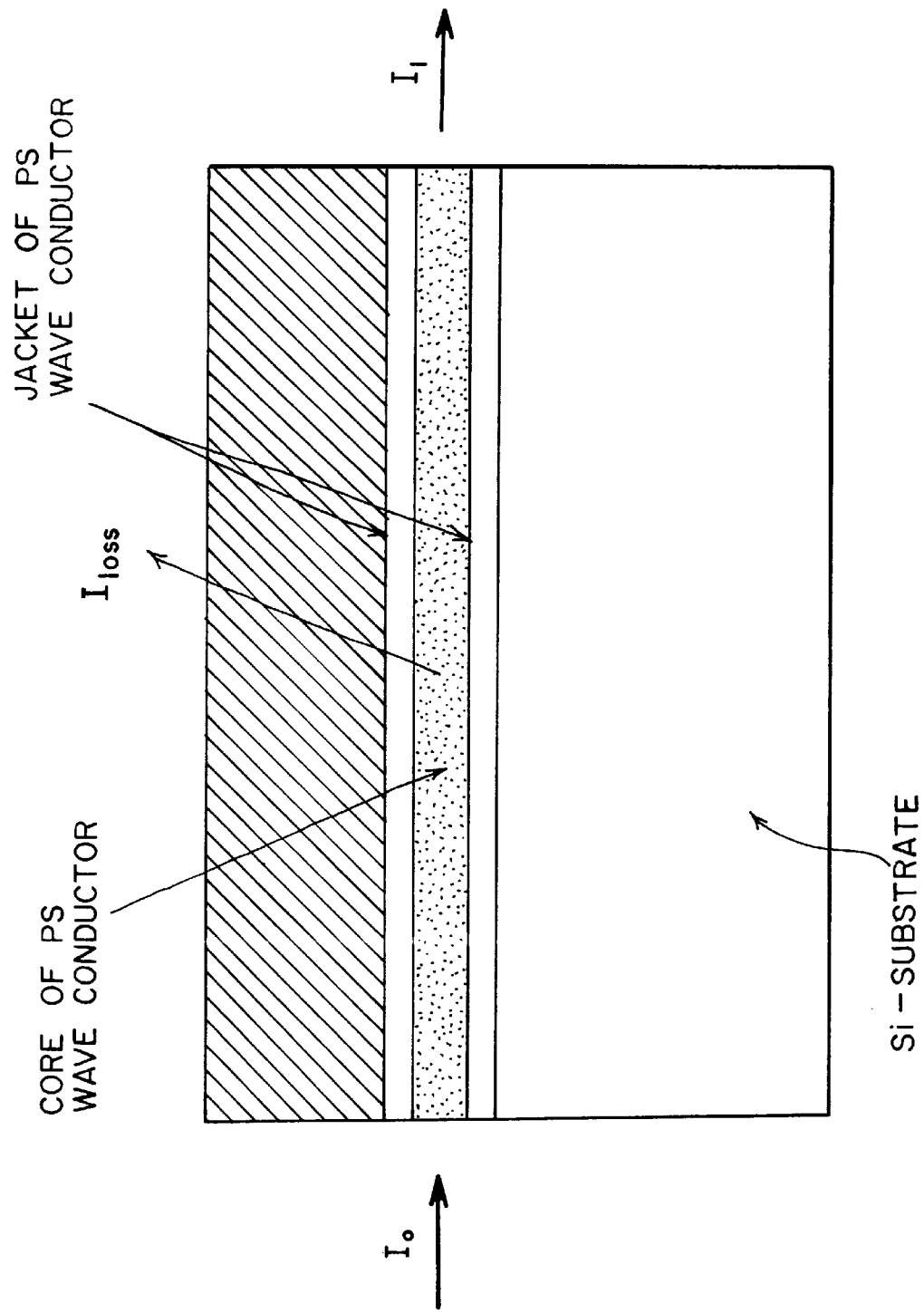
FIG. 4 is a schematic representation of a wave conductor made from porous silicon shown by a cross-sectional view, whereby the quality of adaptation between the core and the jacket of the wave conductor varies depending on the refractive index of the material.

In addition to the manufacture of interference filters, PS is suitable also for producing wave conductors, the properties of which are influenced by the refractive index of the material in the pores as well (FIG. 4). The loss of light intensity, i.e., the ratio of decoupled light intensity $I_1$ to coupled light intensity $I_0$ is, in connection with wave conductors, dependent upon the adaptation of the refractive indices of the core and the jacket of the wave conductor, among other things. With wave conductors made from PS, the core of the PS-wave conductor is produced with a greater volume ratio $V_{Si-crystallites}/V_{pores}$ than the jacket of the wave conductor. Therefore, the refractive index changes less in the core of the wave conductor than in the jacket of the wave conductor if the refractive index of the material in the pores of the PS is varied. The adaptation of the refractive indices of the core and the jacket changes in this way as well, and thus also the loss in light intensity, i.e., with input intensity $I_0$ retained, output intensity $I_1$ is a measure for the refractive index of the material in the pores of the wave conductor.

Embodiment 4: Asymmetric Wave Conductor-Interferometer made from PS

Figure 5:
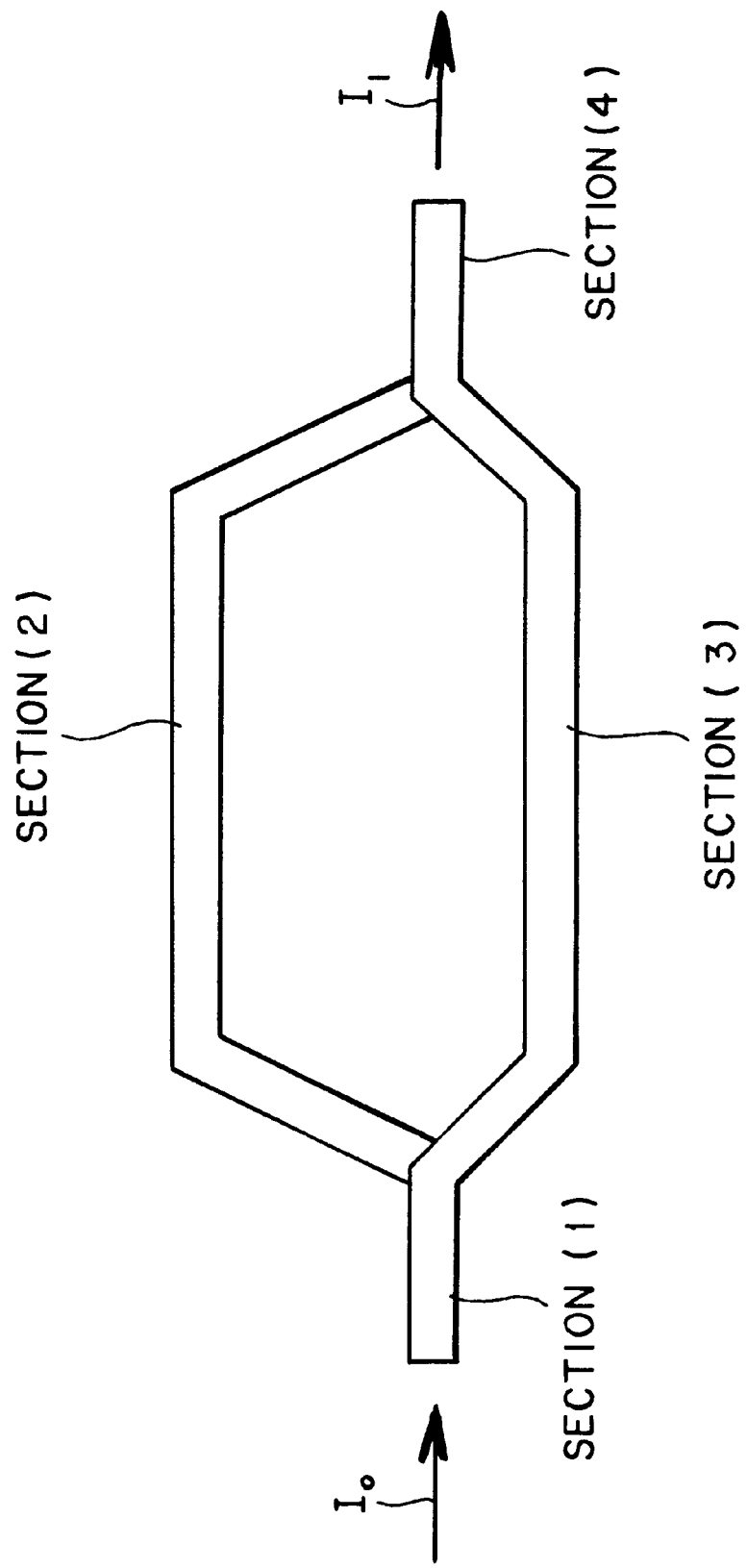
FIG. 5 is a schematic representation of a wave conductor-interferometer shown by a top view, whereby the core and the jacket of the wave conductor are not shown separately for simplification reasons.

FIG. 5 shows an interferometer consisting of wave conductors in which the light beam coupled into a wave conductor section 1 is split into two part beams which, after passing through wave conductor sections 2 or 3, are combined again in a wave conductor section 4. Interference of the part beams occurs in this process, whereby their phase difference is fixed by the lengths of the optical paths, thus by the product of the geometric path length and the refractive index. Such a structure can be used in two ways:

Case "a"

Sections 2 and 3 are both produced from PS, however, they have different geometric lengths. Now, when the refractive index of the material in the pores is altered, the optical path length in sections 2 and 3 changes by the same factor because the refractive index of the PS changes by the same factor. However, the phase difference of the part beams is fixed not by the quotient but by the difference between the optical path lengths in sections 2 and 3. Varying the refractive index of the material in the pores consequently changes the phase difference of the part beams and in this way intensity $I_1$ of the light resulting from the interference of the two part beams.

Case "b"

Either section 2 or section 3 is produced from PS and the other section is made from another material (for example SiGe/Si or Si/insulator). No difference is needed in the length of the sections. Now, if the refractive index of the material in the pores is changed, only the length of the optical path of the PS-wave conductor section changes, whereas the length of the optical path of the other section remains constant. The sensitivity of the component is increased in this way versus case "a". For example, for a PS-wave conductor section of 1 mm length, even a change in the refractive index of the PS of only 0.001 results in a change in the length of the optical path by about 1 $\mu$m, which, when using light with a wavelength of 1 $\mu$m, corresponds with one full period in the interference signal.

Figure 6:
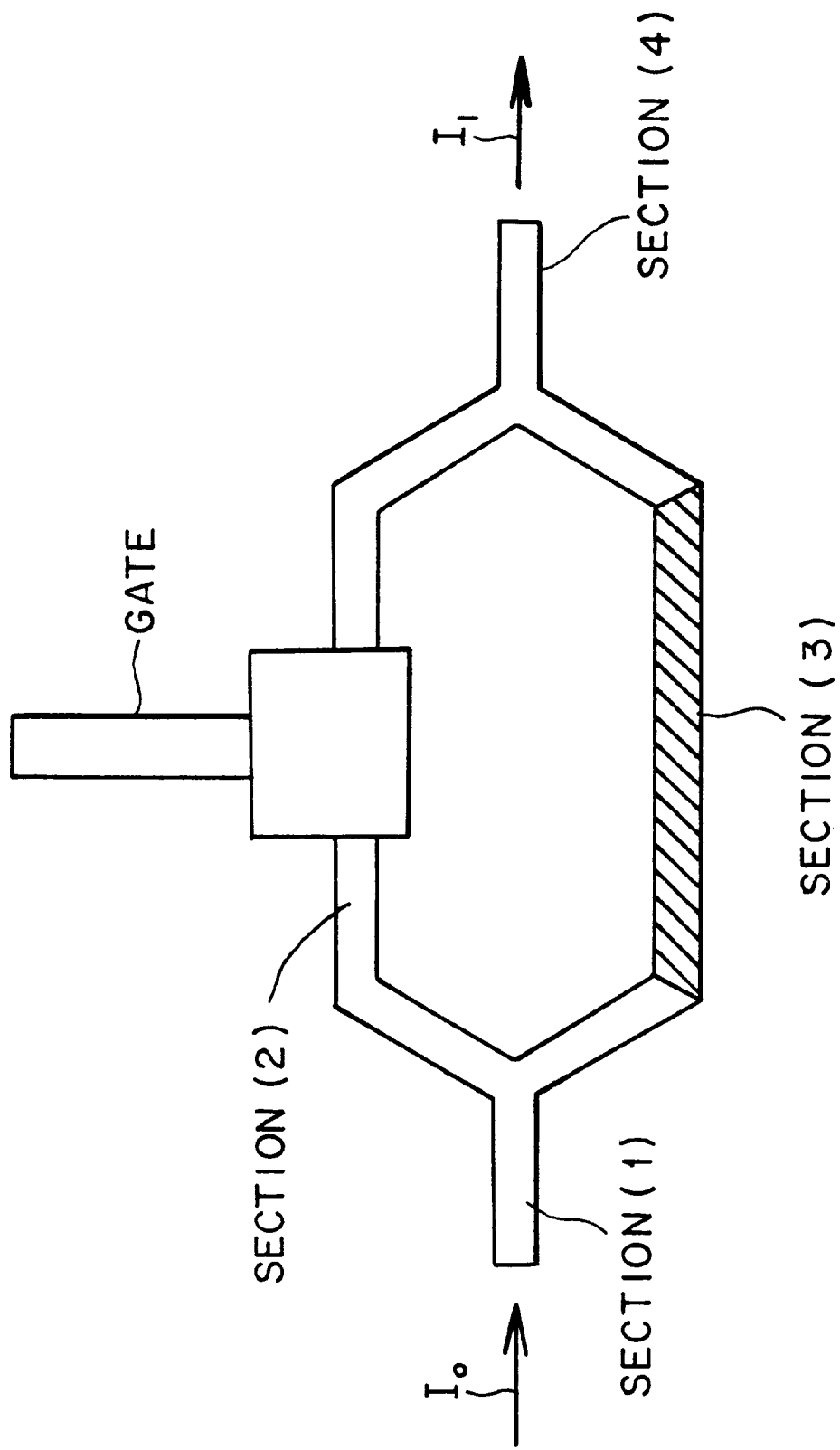
FIG. 6 is a schematic view of a wave conductor-interferometer shown by a top view, with a gate for adjusting a working point, whereby the core and the jacket of the wave conductor are not shown separately for simplification reasons as well.

Embodiment 5: Wave Conductor-Interferometer with Gate for adjusting the Operating Point A problem with the operation of components according to embodiment 4 is that the intensity of the interference signal is fixed for a given pore material by the geometry of the component. In many cases, however, it is necessary to vary the operating point of the component in the course of operation. This may mean, for example, that the decoupled light intensity has to be maximal for a certain pore material. This can be accomplished by attaching to the component according to embodiment 4b a gate above the wave conductor section without PS. This geometry is shown in FIG. 6. The refractive index of the wave conductor underneath can be varied by the voltage applied to the gate and thus it is possible to adjust the phase difference of the part beams. Such a component is referred to as a Mach-Zender-interferometer which, however, is without a variable PS-wave conducyor section.

Expansion of Embodiments 1 to 5

If a diaphragm with selective permeability is applied to the surface of the PS, only substances to which the diaphragm is permeable can penetrate the pores of the PS. Consequently only such substances can lead to a change in the refractive index of the PS. By selecting a suitable diaphragm it is possible in this way to provide the components according to embodiments 1 to 5 with selectivity versus individual substances.

The idea of the invention is described in summary as follows:

(1) Processes in which the presence of substances is detected or their concentration in solvents is determined by the change in the refractive index of PS caused by such substances.

(2) A component in connection with which the optical properties of an interference filter made from PS are determined by the refractive index of the substance to be detected.

(3) The component according to subitem (2), which contains the components "light source", "interference filter" and "light detector". The component may consist of separate components, or several or all components may be integrated on one chip.

(4) A component containing wave conductors made from PS and in which the transmission of light through the wave conductor is varied by the refractive index of the material present in the pores of the PS. In this connection, the wave conductors must not completely consist of PS.

(5) The component according to subitem (4), in connection with which the transmission through one or a plurality of wave conductors made from PS is varied in that a part of the light conducted in the wave conductor is uncoupled due to variation of the difference in the refractive index between the core and the jacket of the wave conductor resulting from the change in the refractive index of the PS.

(6) The component according to subitem (4), in which the light conducted in the wave conductor is split into a plurality of beams and subsequently combined again, so that the part beams interfere with each other. One or several of the part beams are conducted in this connection in wave conductor sections made from PS, so that the length of the optical path of said part beams can be varied via the refractive index of the material in the pores of the PS. This causes a change in the phase difference of the part beams and thus in the intensity of the light beam resulting from interference of said part beams.

(7) The component according to subitem (6), in connection with which Schottky-gates are attached to one or to a plurality of wave conductor sections. The refractive index can be controlled below the gate by the electric voltage applied to said gates and the operating point of the component can thus be adjusted.

(8) The component according to subitems (2) to (6), in connection with which only selected substances are capable of penetrating the pores due to the use of a semipermeable diaphragm on the surface of the PS, which renders the component selective versus the desired substance.

What is claimed is:

1. An analysis instrument for a chemical sensor for producing a variable refractive index, comprising
   a light source and a light receiver and a porous material arranged in a light path between the light source and the light receiver, with a fluid in the porous material, said fluid influencing the refractive index of the porous material,
   said porous material is p-doped silicon with a porous microstructure formed by etching directly in a p-doped silicon substrate, said refractive index is preset and varied in dependence upon the refractive index of the fluid, and
   whereby influencing of the porous material can be used for detecting a substance or for determining the concentration of a substance.

2. The analysis instrument according to claim 1, wherein the chemical sensor is an interference filter illuminated by a light source and coupled with a light detector for detecting a change in the optical property of the interference filter.

3. The analysis instrument according to claim 2, wherein the optical property of the interference filter is variable in dependence upon the structure of the porous silicon.

4. The analysis instrument according to claim 2, wherein the light source is a laser diode and the detector is a photodiode.

5. The analysis instrument according to claim 4, wherein the filter frequency of the interference filter is adapted to the wavelength of the laser.

6. The analysis instrument according to claim 2, wherein the interference filter is a reflecting filter.

7. The analysis instrument according to claim 2, wherein the interference filter is a transmission filter.

8. The analysis instrument according to claim 7, wherein the transmission filter is integrated in a photodiode.

9. The analysis instrument according to claim 1, wherein the chemical sensor is integrated on a microchip.

10. The analysis instrument according to claim 1, wherein the chemical sensor is a wave conductor at least partly consisting of porous silicon.

11. The analysis instrument according to claim 10, wherein a core of the wave conductor has a greater volume ratio than a jacket of the wave conductor.

12. The analysis instrument according to claim 11, wherein the ratio of coupled light efficiency $I_1$ to uncoupled light efficiency $I_0$ is a measure for the refractive index of the substance or of the fluid containing the substance.

13. The analysis instrument according to claim 10, wherein at least two wave conductors form an interferometer, in which at least two part beams of a coupled light beam each pass through a wave conductor section 1, 2, and 3, and produce or generate an interference when combined,
    whereby a phase difference is fixed by given optical path lengths.

14. The analysis instrument according to claim 13, wherein the two wave conductor sections 2,3 consist of porous silicon and have different geometric path lengths.

15. The analysis instrument according to to claim 13, wherein one of the wave conductor sections 2, 3 consists of porous silicon and the other wave conductor section 2 or 3 consists of another material.

16. The analysis instrument according to claim 15, wherein the other material of the other wave conductor section 2 or 3 is either SiGe/Si or Si/insulator.

17. The analysis instrument according to claim 13, wherein a Schottky-gate is attached to at least one wave conductor section 2, 3 in order to vary a working point during operation.

18. The analysis instrument according to claim 10 wherein the optical property of one or more wave conductor section(s) made from porous silicon is variable in dependence upon the structure of the porous silicon.

19. The analysis instrument according to claim 11, wherein a diaphragm with selective permeability is applied to the surface of the porous silicon.

20. The analysis instrument according to claim 1, wherein the refractive index of the porous silicon is selected as the optical property of the porous silicon.

* * * * *